United States Patent [19]

Fujii et al.

[11] Patent Number: 4,689,552
[45] Date of Patent: Aug. 25, 1987

[54] METHOD AND DEVICE FOR DETECTING INSULATION DAMAGE TO A BURIED OBJECT

[75] Inventors: Akihiko Fujii; Masahiro Tsuka, both of Osaka, Japan

[73] Assignee: Osaka Gas Company, Ltd., Osaka, Japan

[21] Appl. No.: 882,012

[22] PCT Filed: Apr. 12, 1983

[86] PCT No.: PCT/JP83/00110
§ 371 Date: Dec. 12, 1984
§ 102(e) Date: Dec. 12, 1984

[87] PCT Pub. No.: WO84/04166
PCT Pub. Date: Oct. 25, 1984

Related U.S. Application Data

[63] Continuation of Ser. No. 687,420, Dec. 12, 1984, abandoned.

[51] Int. Cl.[4] .......................................... G01R 31/12
[52] U.S. Cl. .................................... 324/546; 324/512
[58] Field of Search ................... 324/54, 52, 51, 67, 324/326, 329; 364/483; 340/647, 650, 651

[56] References Cited

U.S. PATENT DOCUMENTS

| 3,800,217 | 3/1974 | Lowrance | 324/54 |
|---|---|---|---|
| 3,916,298 | 10/1975 | Ulrich | 324/67 |
| 4,063,161 | 12/1977 | Pardis | 324/64 |
| 4,099,117 | 7/1978 | Erath | 324/54 |

FOREIGN PATENT DOCUMENTS 46-43589 12/1971 Japan .
49-39942 10/1974 Japan .

OTHER PUBLICATIONS

Kadoi et al, Studies on Soil Corrosion of Metallic Materials (Part 1) Fundamental Experiment on Soils, 1966, pp. 10–18.

*Primary Examiner*—Reinhard J. Eisenzopf
*Assistant Examiner*—Jack B. Harvey
*Attorney, Agent, or Firm*—Wenderoth, Lind & Ponack

[57] ABSTRACT

A method of and an apparatus for detecting damage to a buried object which includes the steps of (a) providing a buried object extending in a longitudinal direction which has an electrically insulating layer over a conductive member, (b) connecting one terminal of a power supply to the conductive member at a first position thereon, (c) connecting the other terminal of the power supply to an ammeter which is grounded, (d) connecting both terminals of at least one voltmeter to the conductive member on each side of the first position with the terminals of each voltmeter being spaced apart in the longitudinal direction, (e) connecting at least one voltmeter and the ammeter to data processing equipment for analyzing output values from the at least one voltmeter and the ammeter when power is supplied to the conductive member from the power supply, (f) supplying electric current from the power supply to the conductive member, and (g) measuring and comparing output values from the ammeter and the at least one voltmeter for detecting the presence of damage to the buried object and the relative location of any damage present as indicated by larger output values from any of the at least one voltmeter connected to the conductive member between the first position and a point of damage to the buried object.

5 Claims, 15 Drawing Figures

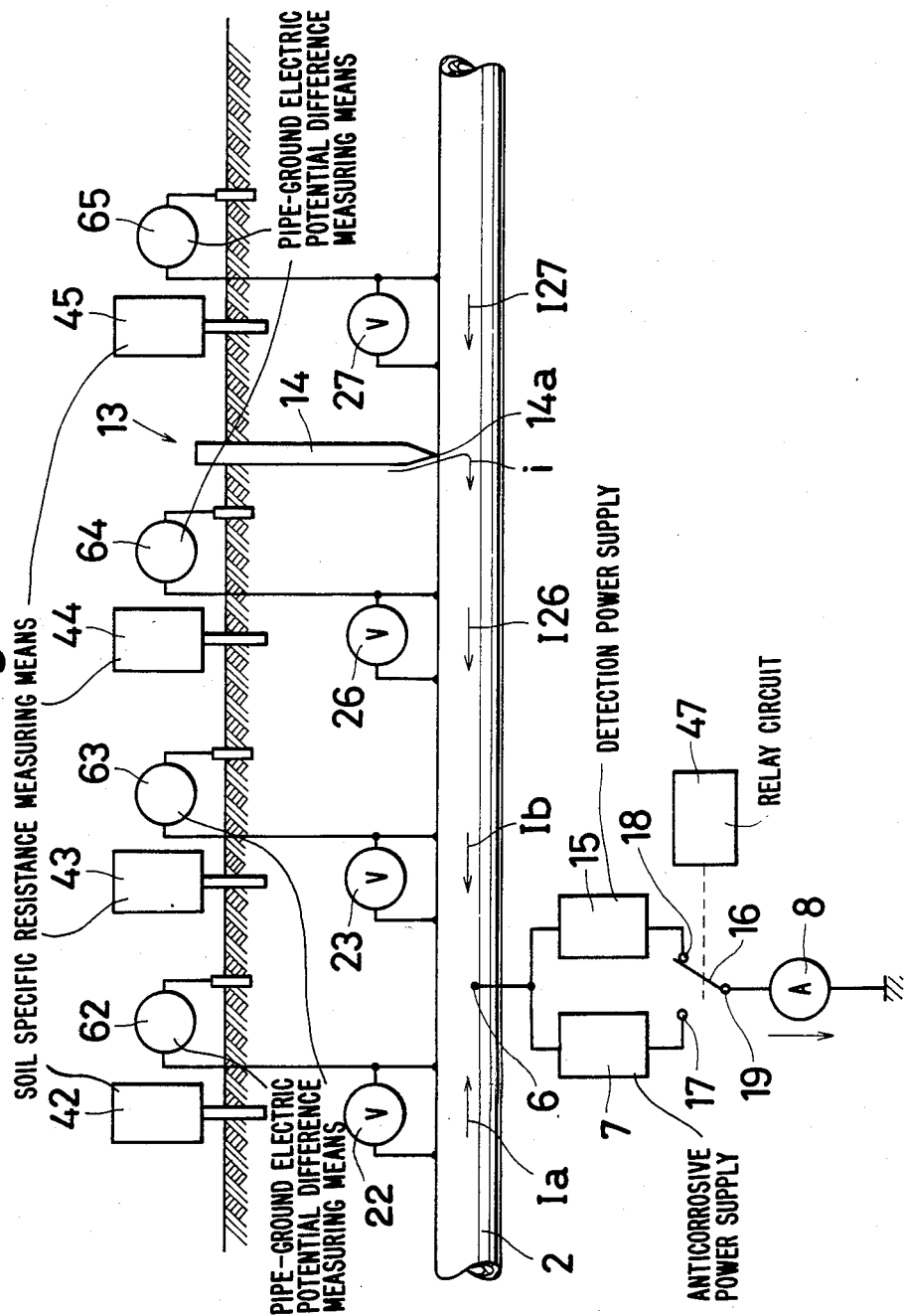

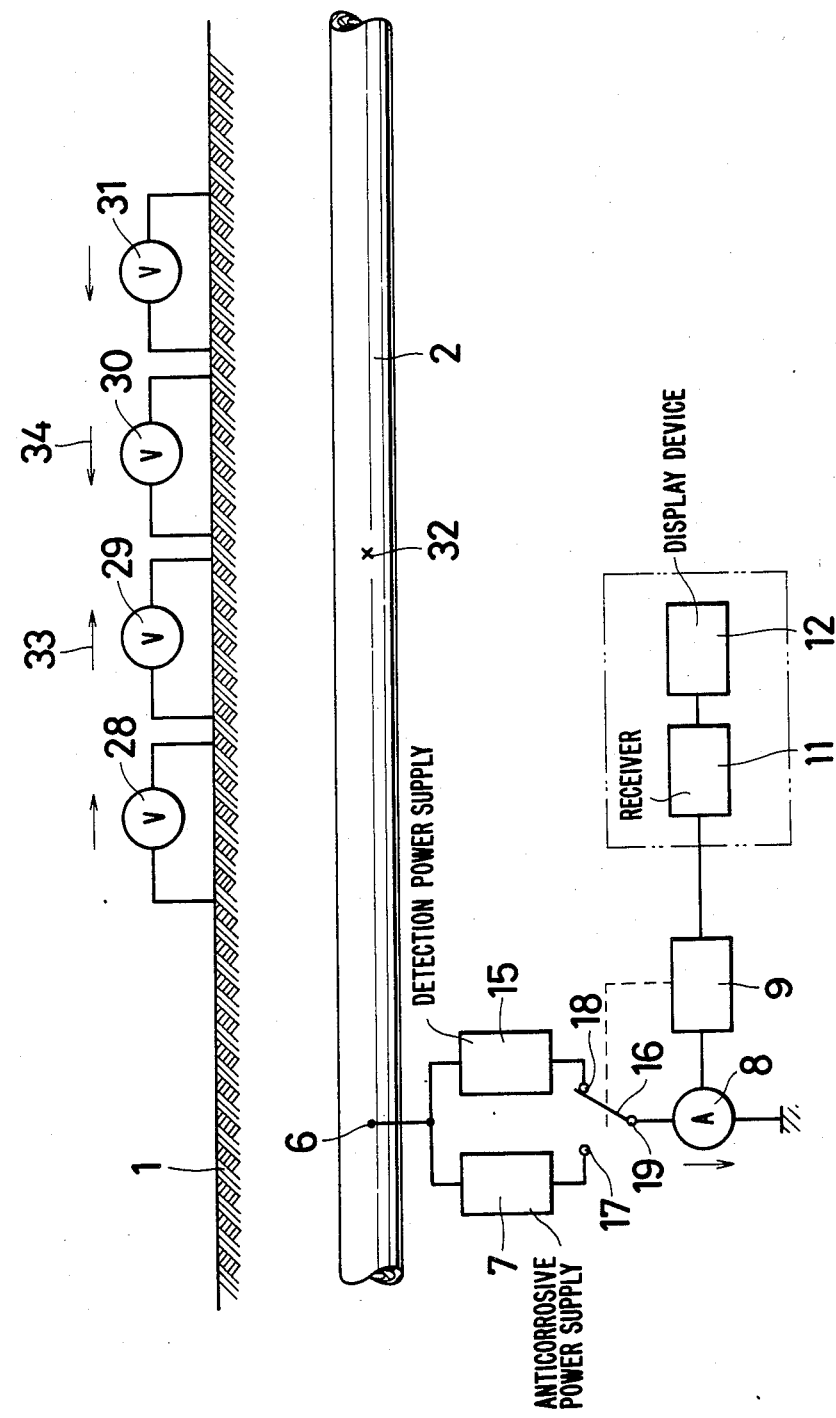

METHOD AND DEVICE FOR DETECTING INSULATION DAMAGE TO A BURIED OBJECT

This application is a continuation of now abandoned application Ser. No. 687,420, filed Dec. 12, 1984, now abandoned.

TECHNICAL FIELD

The present invention relates to a method and apparatus for detecting damage to a buried object covered with an electrically insulating layer over the outer periphery of a conductive member, such as a buried pipe member covered with a coating layer over the outer periphery of a steel pipe.

BACKGROUND OF THE INVENTION

In order to assure sound maintenance of pipes for transporting a fluid, it is essential to prevent surface corrosion as well as damage due to roadwork, etc.

For prevention of surface corrosion, a polyethylene lining for a layer covering the peripheral surface of a steel pipe, has recently been employed, thereby improving greatly the insulating performance or corrosion proof characteristic. Additional provision of electric anticorrosion assures prevention of surface corrosion.

However, damage to a steel pipe due to roadwork etc. on the road surface may cause a leak to occur, resulting in an accident. In order to prevent an accident, the managing agent of a buried object is required to perform extensive monitoring and management tasks such as by patrolling around the buried object or by being present at roadwork performed nearby the buried object. In this connection, immediate detection of pipe damage caused for some reason may help and assist such management, and is very effective for avoiding an accident.

SUMMARY OF THE INVENTION

It is an object of the present invention to provide a method of rapidly detecting damage to a buried object.

It is another object of the present invention to provide a method of detecting the damaged portion of a buried object.

The present invention provides a method of detecting damage to a buried object comprising the steps of flowing an electric current through the conductive member of the buried object covered with an electrically insulating layer over the outer periphery of the conductive member, and comparing the value of such electric current with the value of another electric current measured at a different time so as to detect damage to the buried object.

The present invention also provides a method of detecting damage to a buried object comprising the steps of connecting one terminal of a power supply to the conductive member of a longitudinally extending buried object covered with an electrically insulating layer over the outer periphery of the conductive member, grounding the other terminal of the power supply, and making a comparison between values of electric currents flowing at the same time through the buried object at both sides in the longitudinal direction of the buried object with respect to the portion of the conductive member connected to said one terminal of the power supply so as to detect damage to the buried object.

Furthermore the present invention provides a method of detecting damage to a buried object comprising the steps of connecting one terminal of a power supply to the conductive member of a longitudinally extending buried object covered with an electrically insulating layer, grounding the other terminal of the power supply, making a comparison between values of electric currents flowing at the same time through the buried object at both sides in the longitudinal direction of the buried object with respect to the portion of the conductive member connected to said one terminal of the power supply, and measuring the size of damage to the buried object based on soil specific resistance and a difference of values of electric currents if such difference is detected.

The present invention still also provides a method of detecting damage to a buried object comprising the steps of connecting first terminals of power supplies to a first plurality of connection portions of the conductive member of a longitudinally extending buried object covered with an electrically insulating layer, grounding the other terminals of the power supplies, and making comparisons among values of electric currents flowing at the same time through the conductive member at a second plurality of portions among said first plurality of connection portions so as to detect damage to the buried object.

The present invention provides a device for detecting damage to a buried object covered with an electrically insulating layer over the outer periphery of a conductive member, which comprises a power supply for flowing an electric current through the conductive member and means for making comparisons among values of electric currents flowing at different times.

The present invention also provides a device for detecting damage to a longitudinally extending buried object, which comprises (a) a power supply having one terminal connected to the conductive member and the other terminal grounded, (b) a plurality of electric current detector means for detecting electric currents flowing through the conductive member at both sides in the longitudinal direction of the buried object with respect to the portion of the conductive member connected to said one terminal of the power supply, and (c) means responsive to outputs from the electric current detector means for making a comparison between values of electric currents detected at the same time.

The present invention still also provides a device for detecting damage to a longitudinally extending buried object covered with an electrically insulating layer over the outer periphery of a conductive member comprising (d) a power supply having one terminal thereof connected to the conductive member and the other terminal thereof grounded, (e) a plurality of electric current detector means for detecting electric currents flowing through the conductive member at both sides in the longitudinal direction of the buried object with respect to the portion of the conductive member connected to said one terminal of the power supply, (f) means responsive to outputs from the electric current detector means for making comparisons among values of electric currents detected at the same time, (g) means for detecting specific resistance of soil, and (h) means responsive to the output values from the electric current detector means, the electric current comparing means, and the soil specific resistance detector means, for calculating and measuring the size of damage based on soil specific resistance and a difference between values of electric currents if such difference is detected.

Furthermore the present invention provides a device for detecting damage to a longitudinally extending buried object covered with an electrically insulating layer over the outer periphery of a conductive member comprising (i) power supplies positioned along the buried object at a first plurality of locations and having first terminals thereof connected to the conductive member and the other terminals thereof grounded, (j) a second plurality of means for detecting electric currents flowing through the conductive member at the second plurality of positions among said power-connected portions of the conductive member, and (k) means responsive to outputs from the electric current detector means for making comparisons among values of electric currents detected at the same time.

According to the present invention, a comparison is made between the values of electric currents flowing at different times through a conductive member of a buried object. Therefore, damage to the electrically insulating layer covering the conductive member may be rapidly detected. According to the present invention, furthermore, a power supply is connected to a buried object at a portion of conductive member thereof and a comparison is made between the values of electric currents flowing through the conductive member at both sides in the longitudinal direction of the buried object with respect to the power-connected portion. If damage is caused to the covering layer at one side with respect to the power-connected portion of the conductive member, a larger amount of electric current flows through the conductive member at its damaged side, thus detecting which side of the conductive member with respect to its power-connected portion is damaged.

Moreover, the size of such damage may be calculated and measured bases on soil specific resistance and a difference between pipe electric currents if such difference is detected.

According to the present invention, power supplies are connected to a plurality of portions of the conductive member of a buried object spaced apart in the longitudinal direction of the buried object, and measurement and comparison are made in regard to the values of electric currents flowing at the same time through the conductive member at a plurality of portions among the power-connected portions of the conductive member. If such electric current values are different from one another, this means that the buried object is being damaged. A quick damage detection is thus effected. Moreover, it is understood that damage to a buried object is present between its portions of which electric current values are different from each other. Thus, the portion of damage is assertained.

BRIEF DESCRIPTION OF THE DRAWINGS

FIG. 5 is an underground sectional view of another embodiment of the invention;

FIG. 9 is a sectional view showing a system for detecting a damaged portion 32 of the pipe member 2;

DETAILED DESCRIPTION OF THE PREFERRED EMBODIMENTS

Figure 1:
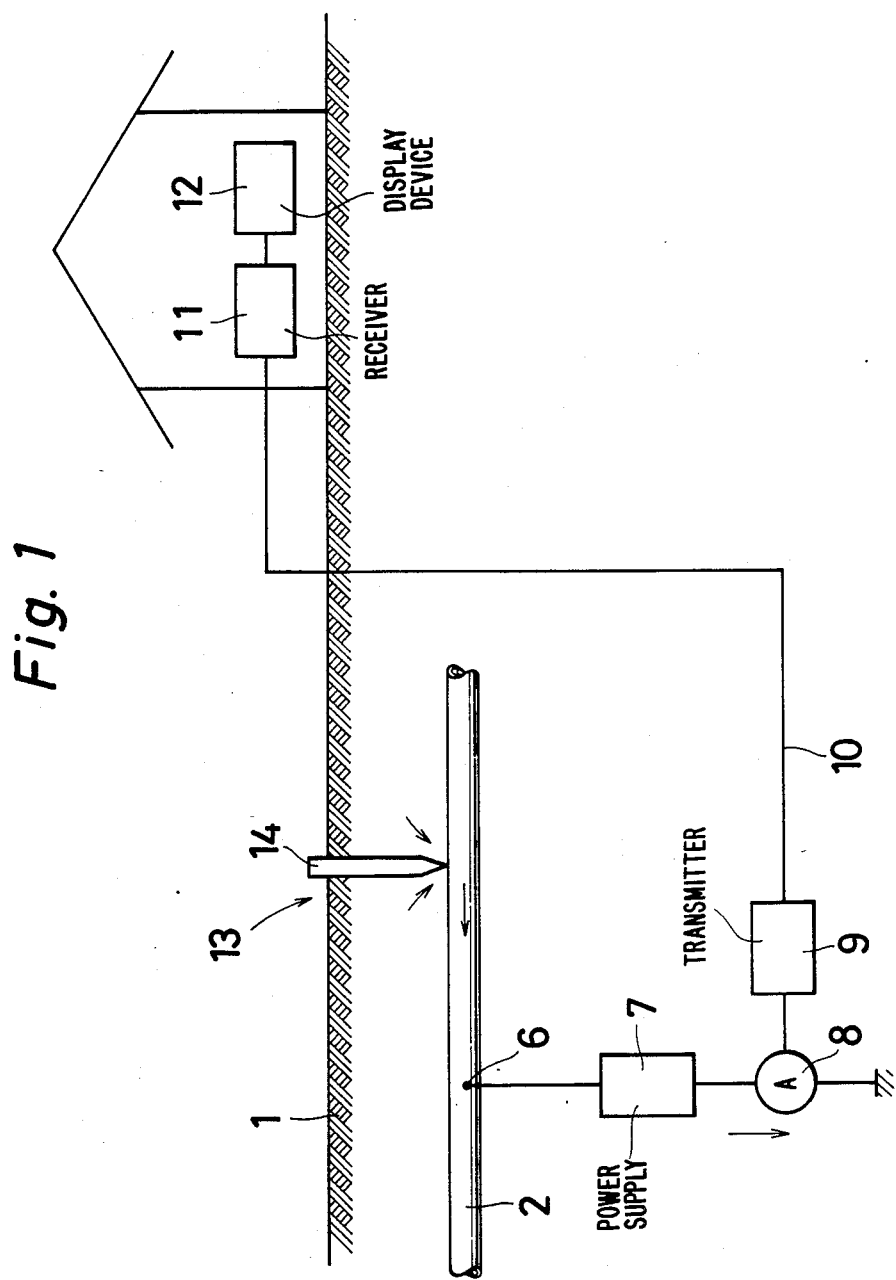
FIG. 1 is an underground sectional view of an embodiment of the present invention.

FIG. 1 is a section view of an embodiment of the present invention.

Figure 2:
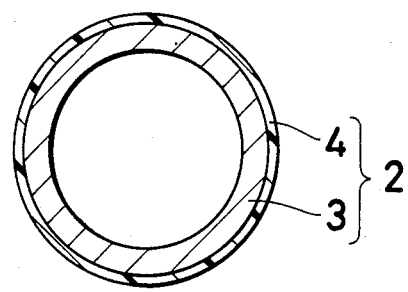
FIG. 2 is a cross section perpendicular to the axis of a pipe member 2.

A pipe member 2 for transporting a fluid is buried under the ground 1. The section of the pipe member 2 perpendicular to the axis thereof is shown in FIG. 2.

Applied to the exterior of a steel pipe 3 of the pipe member 2 is a covering layer 4 made of an electrically insulating material such as polyethylene. This layer 4 covers the steel pipe 3 over its entire periphery along its overall length.

One terminal of an anticorrosive power supply 7 is connected to the portion 6 of the pipe member 2. The other terminal of the power supply 7 is grounded through an ammeter 8. Current values measured by the ammeter 8 are set to a receiver 11 through a transmitter 9 and a transmission line 10, and are displayed by a display device 12. An electric current flows through the steel pipe 3 of the pipe member 2 from the anticorrosive power supply 7, thus providing an electric anticorrosive effect on the pipe member 2.

Where there is no damage to the covering layer 4, an anti-corrosive electric current on the order of, for example, a microampere is measured by the ammeter 8. If small damage is present on the covering layer 4, an electric current in the order of, for example, a milliampere is measured by the ammeter 8.

Figure 3:
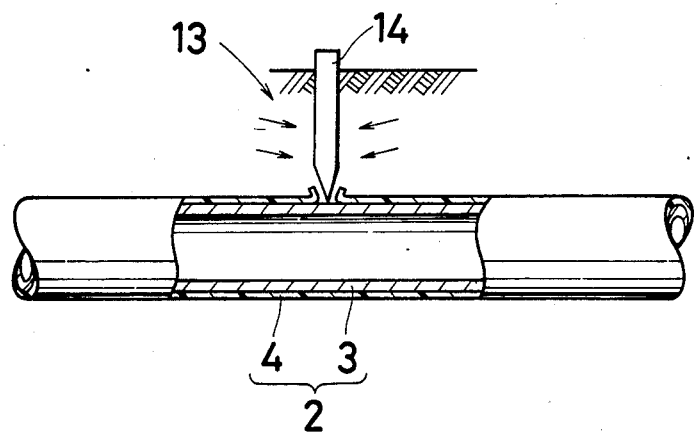
FIG. 3 is a sectional view showing a state of a covering layer 4 damaged by an excavator 14 at a roadwork position 13.
Figure 4:
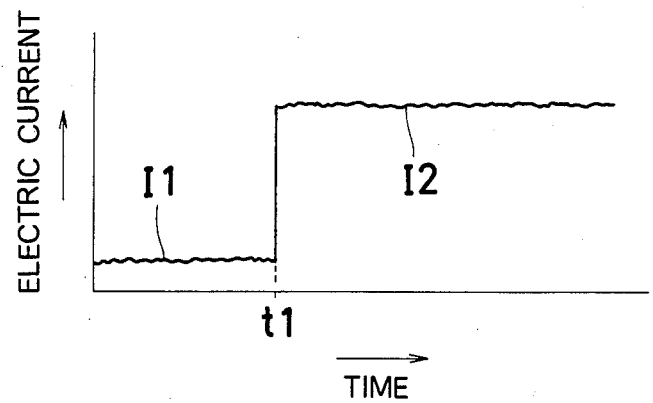
FIG. 4 is a graph showing a change of electric current values with the passage of time which are found by an ammeter 8 of FIG. 1.

It is assumed that a metallic excavator tool 14 inserted into the ground 1 at a roadwork site 13, brakes the covering layer 4 and comes in contact with the steel pipe 3, as clearly shown in FIG. 3. In this case, not only an anticorrosive electric current but also an electric current from the excavator 14 flow through the steel pipe 3. As shown in FIG. 4, a value of the electric current detected by the ammeter 8 is a relatively small value I$_1$ at an ordinary time before the excavator 14 breaks the pipe member 2, but becomes a larger value I$_2$ after the time t1. This means that the pipe member 2 is damaged at the time t1.

Although the anticorrosive power supply 7 is employed in the embodiment discussed hereinbefore, there may be additionally disposed a detection power supply for flowing a larger electric current through the steel pipe 3 for detecting damage to the pipe member 2, and such detection power supply may be used only for periodical detection times, instead of the anticorrosive power supply 7.

FIG. 5 is a section view of another embodiment of the present invention and like numerals are given to the corresponding parts.

In this embodiment, the respective first terminals of the anticorrosive power supply 7 and a detection power supply 15 are connected to the portion 6 in the pipe member 2 of the steel pipe 3. The other terminals of the power supplies 7 and 15 are respectively connected to the contacts 17 and 18 of a changeover switch 16. The common contact 19 of the changeover switch 16 is grounded through the ammeter 8. The changeover switch 16 is actuated by relay circuit means comprising a relay circuit 47.

Figure 6:
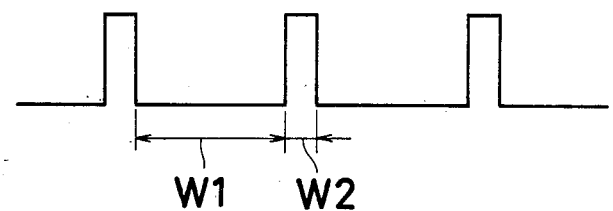
FIG. 6 is a graph showing a change of the value of electric current flowing through the ammeter 8 of FIG. 5.

FIG. 6 shows the wave form of an electric current detected by an ammeter 8. The common contact 19 of the changeover switch 16 is connected to the contact 17 for a period W1, so that an anticorrosive electric current flows through the steel pipe 23 for such period W1.

The common contact 19 of the changeover switch 16 is connected to the contact 18 for a period W2 by the relay circuit 47, so that a large electric current for damage detection is supplied from the detection power supply 15. The period W1 is for example about 10 minutes, while the period time W2 may be, for example, 5 seconds. For the period W2, the detection power supply 15 supplies a large electric current to the steel pipe 3 of the pipe member 2, thus facilitating detection of damage to the pipe member.

Figure 7:
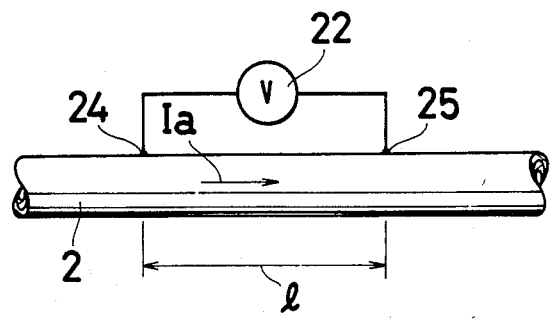
FIG. 7 is an enlarged view showing a state of a voltmeter 22 connected to a buried object 2.

In FIG. 5, a plurality of voltmeters 22 and 23 are connected to the steel pipe 3 of the pipe member 2 for measuring voltages corresponding to the electric currents flowing through the pipe member 2 at both sides in the longitudinal direction thereof with respect to the power-connected portion 6. As shown in FIG. 7, the terminals of the voltmeter 22 are connected by leads to the steel pipe 3 of the pipe member 2 in longitudinally spaced relationship with each other.

An electric current Ia flowing through the steel pipe 3 is expressed by the following equation:

$$Ia = \frac{E}{l \cdot R} \quad (1)$$

where
 E = voltage measured by the voltmeter 22
 l = distance in meter between the portions 24 and 25 of the steel pipe 3 connected to the voltmeters 22. Such distance is for example 30 m.
 R = resistance per meter of the steel pipe 3

Likewise, the voltmeter 23 is connected to the steep pipe 3, thereby measuring the voltage corresponding to the value of electric current Ib flowing through the steel pipe 3. One or a plurality of voltmeters 26, 27, . . . may be additionally connected to the steel pipe 3 of the pipe member 2.

There are provided means for measuring soil specific resistance 42, 43, 44, and 45 at the positions corresponding to the pipe electric current measuring portions where the voltmeters 22, 23, 26 and 27 are disposed. There are also provided means for measuring pipe-ground electric potential difference 62, 63, 64, and 65 corresponding to the voltmeters 22, 23, 26, and 27.

Figure 8:
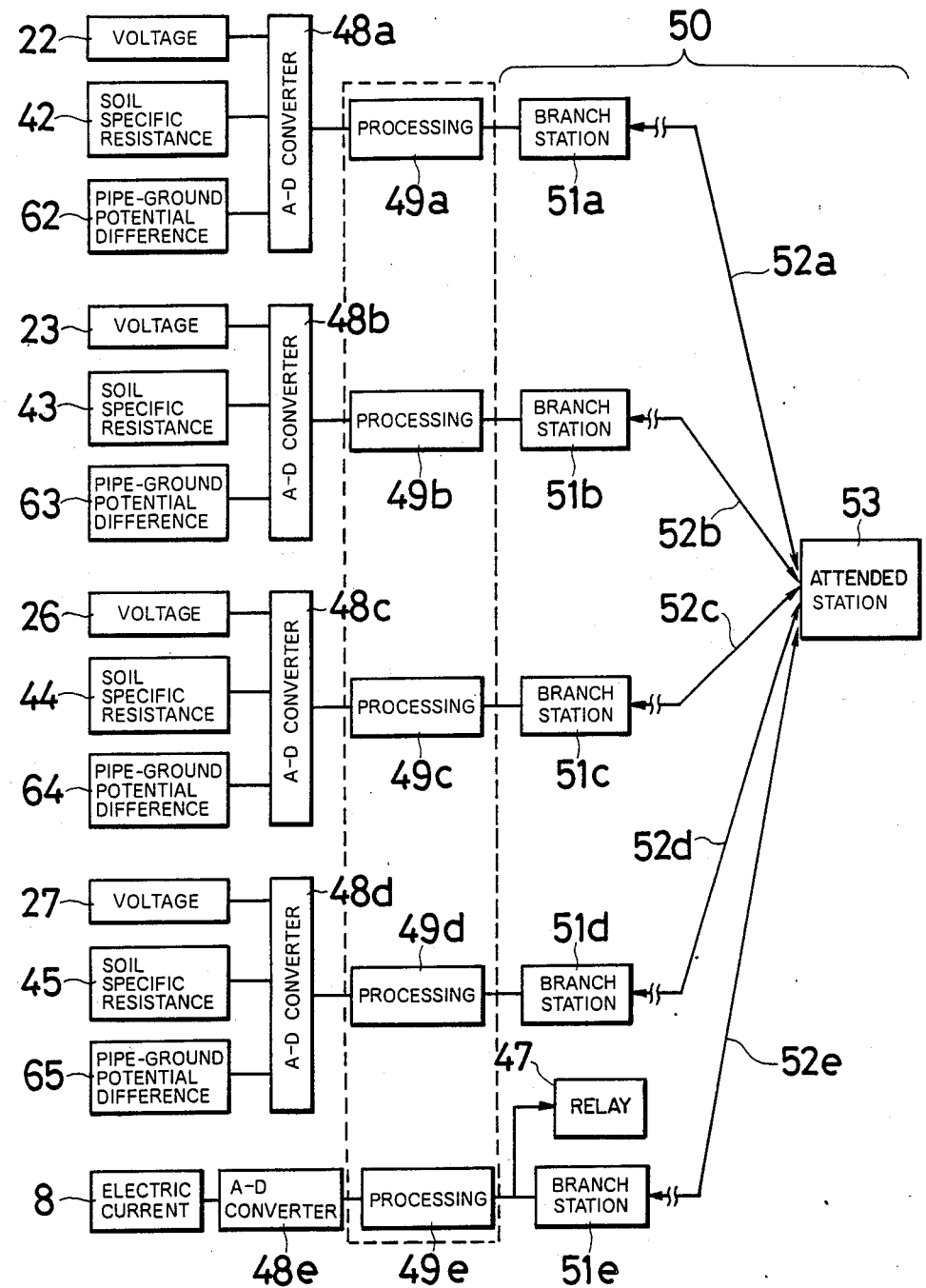
FIG. 8 is a block diagram illustrating an electrical arrangement of the invention.

FIG. 8 shows a block diagram showing an electric arrangement. Respective output values from the voltmeters 22, 23, 26, and 27, the ammeter 8, and the soil specific resistance measuring means 42, 43, 44, and 45 are converted into digital values by an analog-to-digital converter 48, and then sent to a data processing circuit 49 comprising a microcomputer. The data processing circuit 49 samples and measures voltages, electric currents, and soil specific resistances at a plurality of times for the period W2, so as to calculate and measure the average, and maximum and minimum values of those respective values. Output data from the data processing circuit 49 are transmitted to a remote supervisory control device 50.

This remote supervisory control device 50 comprises telemeter branch station 51 for transmitting output data from the data processing circuit 49, a transmission line 52, and a telemeter attended station 53 for performing a control operation. A signal from the telemeter attended station 53 causes the telemeter branch station 51 to switch the changeover switch 16 through the relay circuit 47.

The reference numerals 48, 49, 51, and 52 designate the respective members in the gross with the additive small letters a, b, c, d, and e omitted.

It is assumed that the metallic excavator 14 inserted into the ground 1 at the roadwork site 13, breaks the covering layer 4 of the pipe member 2 and comes in contact with the steel pipe 3. In this case, a large electric current flows through the steel pipe 3 from the excavator 14. Such electric current exhibits a large value between the excavator 14 and the power-connected portion 6 of the pipe member 2, while an electric current flowing through the other portions of the steel pipe 3 is small. That is, the values of electric currents Ib flowing through the steel pipe 3 corresponding to the voltages measured at the same time by the voltmeters 23 and 26 are large and equal to each other. On the other hand, the value of an electric current Ia flowing through the steel pipe 3 corresponding to the voltages measured by the voltmeter 22 is small and the value of an electric current flowing through the steel pipe 3 corresponding to the voltages measured by the voltmeter 27 is also small. When a comparison is made between the electric currents Ia and Ib flowing through the steel pipe 3 corresponding to the voltage measured by the voltmeters 22 and 23 which are disposed at both sides of the pipe member 2 in the longitudinal direction thereof with respect to the power-connected portion 6, the value of the electric current Ib flowing through the steel pipe 3 corresponding to the voltage measured by the voltmeter 23 is larger than Ia. This means that the pipe member 2 is being damaged at the right side in FIG. 5 or at the side of the voltmeter 23 which has detected the voltage corresponding to the larger electric current, with respect to the power-connected portion 6. Moreover, since the electric current values corresponding to voltages measured by the voltmeters 26 and 27 are different from each other, it is readily understood that the damage is present on the pipe between these voltmeters 26 and 27.

It is assumed that the pipe-ground electric potential difference on the ground corresponding to the damaged portion 14a of the pipe member 2 is indicated as V and the damage shape of the damaged portion 14a is a circle having a radius r. Where the damage radius r is sufficiently larger than the covering layer thickness t, the damage radius r or the damage size is approximated based on the following equation:

$$r \text{ (meters)} = k \frac{i \text{ (amps)} \rho \text{ (ohm-meter)}}{V \text{ (volts)}} \quad (2)$$

where $\rho$ = correction coefficient with respect to soil specific resistance of the damaged portion 14a (units = $\Omega \cdot m$)

i = electric current flowing through the steel pipe 3 at the damaged portion 14a (units = A)

V = the average of pipe-ground electrical potential differences on the ground at both sides of the damaged portion 14a (units = V)

k = proportional constant (no units)

Although V undergoes a change with the passage of time, the average of V for the period W2 is substantially constant regardless of time. Therefore, pipe-ground electric potential differences V1 and V2 are measured at suitable time intervals by measuring means 64 and 65 disposed at the pipe electric current measuring points at both sides with respect to the damaged portion 14a, and the average of V1 and V2 is used as V for the equation 2. Such calculation is made by the telemeter attended station 53. The period W2 during which such sampling is made, a determined to be for example about 10 minutes.

$\rho$ varies with the place and the weather. Where the pipe electric current measuring distance is determined to be a suitable one, for example several kilometers, $\rho$ varies with only the weather. If, therefore, soil specific resistance is measured at each of the pipe electric current measuring points, the correction coefficient with respect to soil specific resistance $\rho$ of the pipe member 2 at a given portion is represented by the average of correction coefficients with respect to soil specific resistance values $\rho 1$ and $\rho 2$ measured at the pipe electric current measuring points on both sides with respect to said given portion. Such calculation is made by the telemeter attended station 53.

The electric current i is found from the following equation:

$$i = I26 - I27 \quad (3)$$

where

I26 = electric current flowing through the steel pipe 3 corresponding to the voltage measued by the voltmeter 26 at one side with respect to the damaged portion 14a I27 = electric current flowing through the steel pipe 3 corresponding to the voltage measured by the voltmeter 27 at the other side with respect to the damaged portion 14a The telemeter attended station 53 compares the values of pipe electric currents corresponding to the voltages measured at the substantially same time by the voltmeters 22, 23, 26, and 27 with the respective adjacent ones, based on the results measured for respective periods W2 by the data processing circuit 49. As the consequence of such comparison, if the pipe electric currents I26 and I27 corresponding to the voltages measured by the voltmeters 26 and 27 are different from each other, the size of damage is calculated, measured, and displayed based on the difference i between the electric current values I26 and I27.

Thus calculated damage size depends on the contact area of the excavator 14 with the ground and is larger than the real size of the damage of the pipe member 2, if the excavator 14 remains in contact with the steel pipe 3 and is electrically connected thereto. However, such contact of the excavator 14 with the steel pipe 3 is generally made for a short period of time, for example such as a moment. In this connection, the calculated damage size may be regarded as a value corresponding to the real size of the damage of the pipe member 2, for practical purposes, in view of the fact that the electric current value i is averaged with the passage of time.

FIG. 9 is a section view for precisely detecting the damage position of the pipe member 2. This embodiment is similar to the previous embodiment, and like reference numerals are given to the corresponding parts.

A plurality of voltmeters 28, 29, 30, and 31 provided on the surface of the earth or ground 1 at a plurality of positions in the longitudinal direction of the pipe member 2. Both the terminals of each of these voltmeters 28, 29, 30, and 31 are inserted into the ground 1 at different portions spaced apart along the longitudinal direction of the pipe member 2. An electric current is supplied to the steel pipe 3 of the pipe member 2 from either the anticorrosive power supply 7 or the detection power supply 15, by the changeover switch 16 performing the changeover operation.

Figure 10:
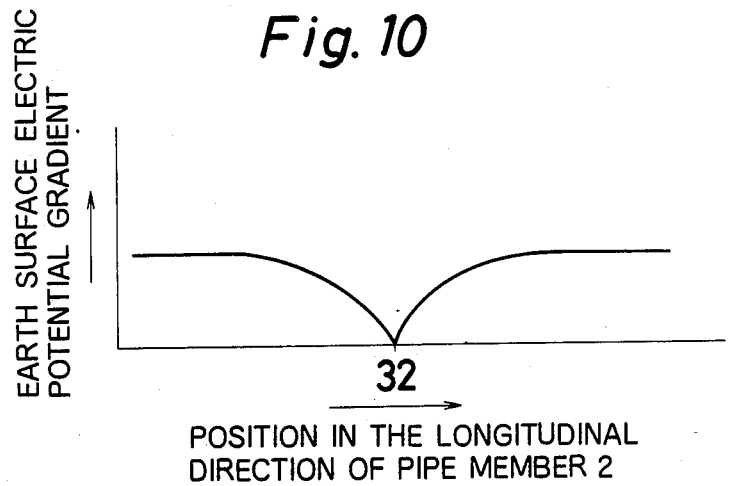
FIG. 10 is a graph showing an electric potential gradient of the earth surface along the longitudinal direction of the pipe member 2.

If the covering layer 4 is damaged at a portion 32 due to roadwork or the like, the voltages detected by the voltmeters 28, 29, 30, and 31 become opposite in polarity on both sides in the longitudinal direction of the pipe member 2 with respect to the damaged portion 32 of the pipe member 2, as shown by arrows 33 and 34 in FIG. 9. Electric potential difference or earth surface electric potential gradient per unit distance of the pipe member 2 in its longitudinal direction measured by the voltmeters 28, 29, 30, and 31, is as shown in FIG. 10. That is, the electric potential gradient becomes extremely small at the damaged portion 32. This means that the covering layer 4 is damaged at a portion exhibiting the small electric potential gradient.

In this embodiment also, a larger electric current is supplied to the steel pipe 3 from the detection power supply 15, thus facilitating measurement utilizing the voltmeters 28, 29, 30, and 31.

The present invention is not limited in application to the buried pipe member 2 discussed hereinbefore, but may be widely applied to buried objects covered with electrically insulating layers over the outer peripheries of conductive members.

The detection power supply 15 used for detecting damage to a buried object may be an AC power supply. In such case, both the terminals of each of the voltmeters 28, 29, 30, and 31 are not necessarily inserted into the ground 1. Search coils may be disposed adjacent to the earth surface, and AC voltages induced by the coils may be measured.

Figure 11:
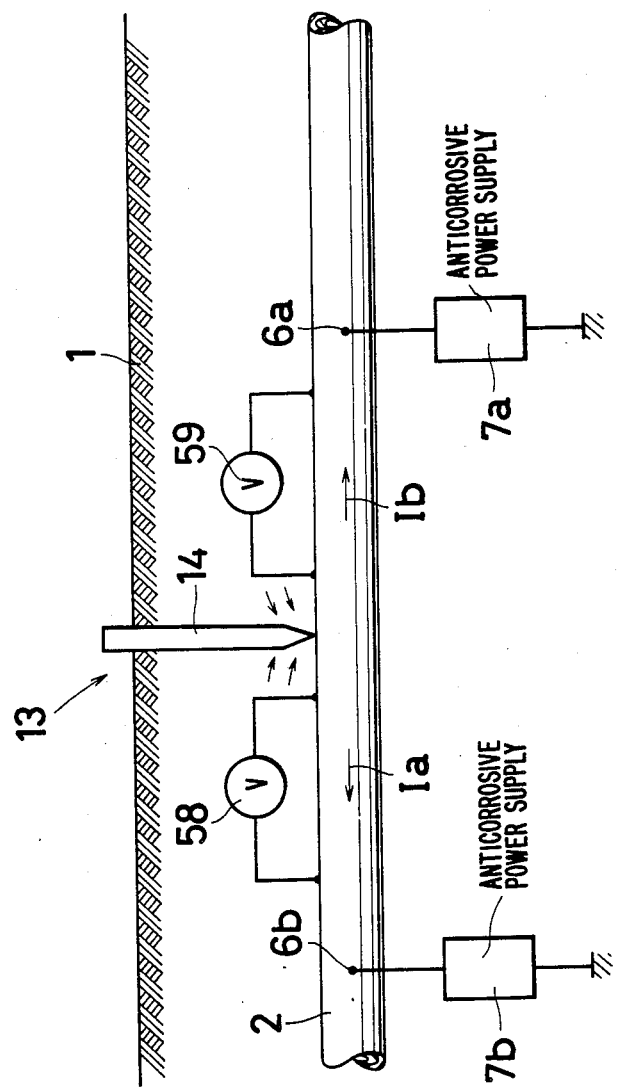
FIG. 11 is an underground sectional view of still another embodiment of the invention.

FIG. 11 is a sectional view of still another embodiment of the present invention.

A pipe member 2 for transporting a fluid is buried under the ground 1. There is connected to portions 6a and 6b of the pipe member 2 one terminal of anticorrosive power supplies 7a and 7b, respectively, of which the other terminals are grounded.

There are provided voltmeters 58 and 59 for measuring voltages corresponding to the values of electric currents Ia and Ib at the same time and comparing with each other through the steel pipe 3 at a plurality of positions (2 positions in this embodiment) among the power-connected portions 6a and 6b.

Figure 12:
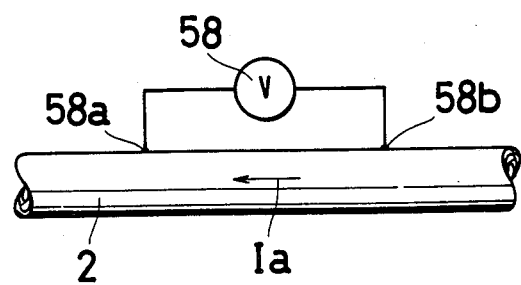
FIG. 12 is an enlarged view showing a state of a voltmeter 58 connected to the buried object 2.

As shown in FIG. 12, the terminals 58a and 58b of the voltmeter 58 are connected to the steel pipe 3 in longitudinally spaced relationship with each other.

An electric current Ia flowing through the steel pipe 3 of the pipe member 2, is expressed by the following equation:

$$Ia = \frac{E}{l \cdot R} \quad (4)$$

where
E = voltage measured by the voltmeter 58
l = distance in meters between the connection portions 58a and 58b
R = resistance per meter of the steel pipe 3.

Figure 13:
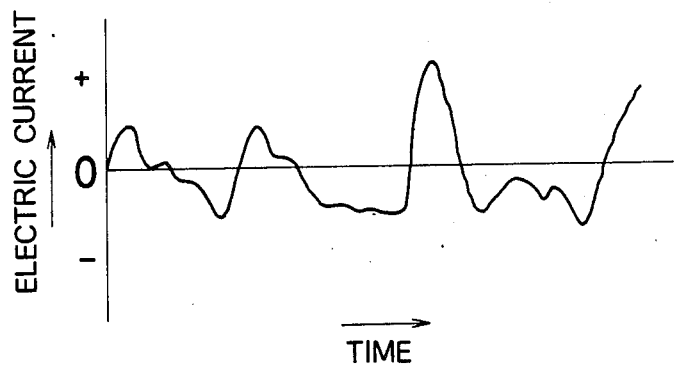
FIG. 13 is a waveform diagram of electric currents I$a$ and I$b$.
Figure 14:
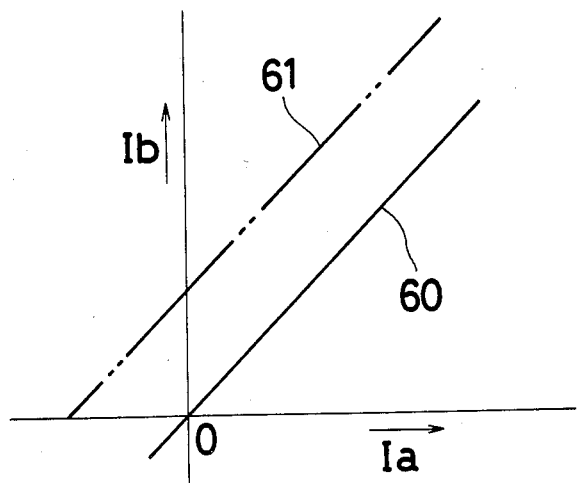
FIG. 14 is a graph illustrating the relationship between values of electric currents I$a$ and I$b$ flowing at the same time.

Likewise, the voltmeter 59 is connected to the steel pipe 3, thus measuring the voltage corresponding to an electric current Ib flowing through the steel pipe 3.

Where the covering layer 4 of the pipe member 2 is not damaged, the values of voltages corresponding to electric currents flowing through the steel pipe 3 measured by the voltmeters 58 and 59 are equal to each other, and undergo a change with the passage of time, for example, as shown in FIG. 13. When these electric currents Ia and Ib are shown in rectangular coordinates, a straight line 60 having a gradient of 45° is found as shown in FIG. 14.

Figure 15:
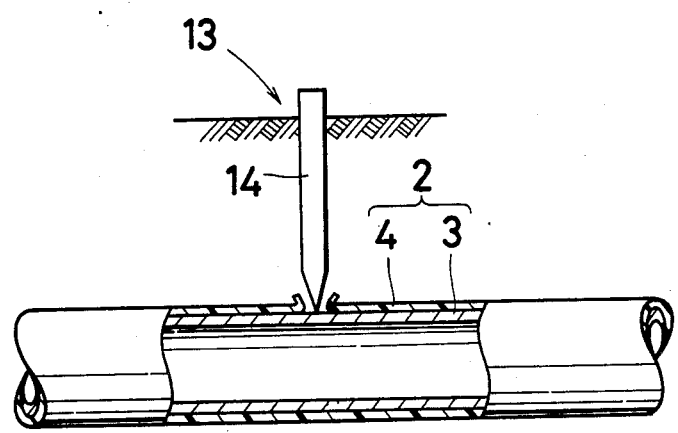
FIG. 15 is an enlarged sectional view showing the buried object 2 when it is damaged at a roadwork position 13.

It is assumed that the metallic excavator 14 inserted in the ground 1 at the roadwork site 13 between the voltmeters 58 and 59 breaks the covering layer 4 of the pipe member 2 and makes contact with the steel pipe 3. In this case, a large electric current flows through the steel pipe 3 from the excavator 14. Such electric current branches off at different rates to the right- and left-sides of the steel pipe 3 with respect to the roadwork site 13 in FIGS. 11 and 15. Therefore the values of electric currents Ia and Ib corresponding to voltages found at the same time by the voltmeters 58 and 59, are different from each other. As shown in FIG. 14, a set of measured electric currents (Ia, Ib) is distrubuted on a line 61 moved in parallel from the line 60 passing through the origin O. Thus it is understood that the pipe member 2 is damaged between its portions connected to the voltmeters 58 and 59. The distance between the voltmeters 58 and 59 may be, for example, 2 to 15 km.

In this embodiment, anticorrosive electric currents flowing through the steel pipe 3 of the pipe member 2 interact with each other in view of the fact that a plurality of power supplies 7a and 7b are disposed, and such electric currents are greatly affected by stray electric currents in the ground. Thus, the state of such electric currents becomes as shown in FIG. 13. In this connection, it is difficult to detect whether or not the covering layer 4 is damaged, by discriminating the respective levels of the current values Ia and Ib. However, in the above-mentioned embodiment, an accurate detection of damage to the covering layer 4 may be executed even if the electric currents Ia and Ib detected at the same time are greatly changed.

According to yet another embodiment of the present invention, damage detection power supplies for supplying greater electric currents than those of the anticorrosive power supplies 7a and 7b, are respectively provided for the power supplies 7a and 7b. Such damage detection power supplies are periodically switched over to the power supplies 7a and 7b, thus facilitating measurement utilizing the voltmeters 58 and 59.

The present invention is not limited in application to the buried pipe member 2, but may be widely applied to longitudinally extending buried objects covered with electrically insulating layers over the outer peripheries of conductive members.

What is claimed is:

1. A method of detecting damage to a buried object comprising the steps of:
   providing a buried object extending in a longitudinal direction, said object having an electrically insulating layer over a conductive member;
   connecting one terminal of a power supply to said conductive member at a first position thereon;
   connecting the other terminal of said power supply of an ammeter which is grounded;
   supplying electric current from said power supply to said conductive member; and
   sending signals from said ammeter to a display device to indicate damage to said buried object when electric current measured by said ammeter increases from a value which corresponds to a value of electric current measured by said ammeter when said object is not damaged.

2. A method of detecting damage to a buried object comprising the steps of:
   providing a buried object extending in a longitudinal direction, said object having an electrically insulating layer over a conductive member;
   connecting one terminal of a power supply to said conductive member at a first position thereon;
   connecting the other terminal of said power supply to an ammeter which is grounded;
   connecting both terminals of at least one first voltmeter to said conductive member on one side of said first position and connecting both terminals of at least one second voltmeter to said conductive member on the other side of said first position with said terminals of said at least one first voltmeter and said terminals of said at least one second voltmeter being spaced apart in said longitudinal direction;
   connecting said at least one first voltmeter, said at least one second voltmeter and said ammeter to data processing means for analyzing output values from said at least one first voltmeter, said at least one second voltmeter and said ammeter when power is supplied to said conductive member from said power supply;
   supplying electric current from said power supply to said conductive member; and
   measuring and comparing output values from said ammeter, said at least one first voltmeter and said at least one second voltmeter for detecting the presence of damage to said buried object and the relative location of any damage present as indicated by larger output values from said at least one first voltmeter or said at least one second voltmeter connected to said conductive member between said first position and a point of damage of said buried object.

3. A method of detecting damage to a buried object comprising the steps of:
   providing a buried object extending in a longitudinal direction, said object having an electrically insulating layer over a conductive member;
   connecting one terminal of a power supply to said conductive member at a first position thereon;

connecting the other terminal of said power supply to an ammeter which is grounded;

connecting both terminals of at least one first voltmeter to said conductive member on one side of said first position and connecting both terminals of at least one second voltmeter to said conductive member on the other side of said first position with said terminals of said at least one first voltmeter and said terminals of said at least one second voltmeter being spaced apart in said longitudinal direction;

connecting soil specific resistance measuring means to soil located at each position corresponding to said at least one first voltmeter and said at least one second voltmeter;

connecting said at least one first voltmeter, said at least one second voltmeter, said soil specific measuring means and said ammeter to data processing means for analyzing output values from said at least one first voltmeter, said at least one second voltmeter and said ammeter when power is supplied to said conductive member from said power supply;

supplying electric current from said power supply to said conductive member; and measuring and comparing output values from said ammeter, said soil specific resistance measuring means, said at least one first voltmeter and said at least one second voltmeter for detecting the presence of damage to said buried object and the relative location of any damage present as indicated by larger output values from said at least one first voltmeter or said at least one second voltmeter connected to said conductive member between said first position and a point of damage of said buried object.

4. A method of detecting damage to a buried object comprising the steps of:

providing a buried object extending in a longitudinal direction, said object having an electrically insulating layer over a conductive member;

connecting one terminal of a power supply to said conductive member at a first position thereon;

connecting the other terminal of said power supply to an ammeter which is grounded;

connecting both terminals of at least one first voltmeter to said conductive member on one side of said first position and connecting both terminals of at least one second voltmeter to said conductive member on the other side of said first position with said terminals of said at least one first voltmeter and said terminals of said at least one second voltmeter being spaced apart in said longitudinal direction;

connecting soil specific resistance measuring means to soil located at each position corresponding to said at least one first voltmeter and said at least one second voltmeter;

connecting pipe-ground electric potential difference measuring means at each position corresponding to said at least one first voltmeter and said at least one second voltmeter;

connecting said at least one first voltmeter, said at least one second voltmeter, said soil specific resistance measuring means, said pipe-ground electric potential difference measuring means and said ammeter to data processing means for analyzing output values from said at least one first voltmeter, said at least one second voltmeter and said ammeter when power is supplied to said conductive member from said power supply;

supplying electric current from said power supply to said conductive member; and measuring and comparing output values from said ammeter, said soil specific resistance measuring means, said pipe-ground electric potential difference measuring means, said at least one first voltmeter and said at least one second voltmeter for detecting the presence of damage to said buried object and the relative location of any damage present as indicated by larger output values from said at least one first voltmeter or said at least one second voltmeter connected to said conductive member between said first position and a point of damage of said buried object.

5. A device for detecting damage to a buried object which includes an electrically insulating layer over the outer periphery of a conductive member, comprising:

an anticorrosive power supply having a pair of terminals, one of said terminals being connected to a portion of said conductive member;

a detection power supply having a pair of terminals, one of said terminals being connected to said portion of said conductive member;

a changeover switch having one contact connected to the other one of said terminals of said anticorrosive power supply and said changeover switch having another contact connected to the other one of said terminals of said detection power supply, said one contact and said other contact being selectively connected to a common contact of said changeover switch;

relay circuit means connected to said changeover switch for selectively connecting said one contact or said other contact to said common contact;

an ammeter connected to said common contact of said changeover switch;

a plurality of voltmeters, each of said voltmeters having a pair of terminals connected to said conductive member with each terminal being spaced apart along the length of said conductive member, at least one of said voltmeters being connected to said conductive member on either side of said portion of said conductive member;

a plurality of means for measuring soil specific resistance each of which is located at a position corresponding to a respective one of said plurality of voltmeters;

a plurality of means for measuring pipe-ground electric potential difference each of which is located at a position corresponding to a respective one of said plurality of voltmeters;

a plurality of analog to digital converters each of which is connected to a respective one of said voltmeters and said ammeter, a respective one of said means for measuring soil specific resistance and a respective one of said means for measuring pipe-ground electric potential difference;

a plurality of data processing circuits each of which is connected to a respective one of said plurality of analog to digital converters;

a remote supervisory control device connected to each of said plurality of data processing circuits for controlling operation of said changeover switch and analyzing data from said data processing circuits to determine the presence of damage to said buried object and the extent of any damage detected.

* * * * *